United States Patent [19]

Takamizawa et al.

[11] 4,337,348

[45] Jun. 29, 1982

[54] BENZOIN GROUP-CONTAINING CYCLIC ORGANOPOLYSILOXANES AND A METHOD FOR THE PREPARATION THEREOF

[75] Inventors: Minoru Takamizawa, Annaka; Fumio Okada, Takasaki; Hisashi Aoki, Annaka, all of Japan

[73] Assignee: Shin-Etsu Chemical Company Limited, Tokyo, Japan

[21] Appl. No.: 274,631

[22] Filed: Jun. 17, 1981

[30] Foreign Application Priority Data

Jun. 20, 1980 [JP] Japan ................................. 55-83520

[51] Int. Cl.$^3$ .............................................. C07F 7/18
[52] U.S. Cl. ................................ 556/436; 106/287.13
[58] Field of Search ......................................... 556/436

[56] References Cited

U.S. PATENT DOCUMENTS 3,636,026 1/1972 Fuhr et al. .......................... 556/436
4,273,907 6/1981 Takamizawa et al. .......... 556/436 X

FOREIGN PATENT DOCUMENTS 54-44643 4/1979 Japan .................................. 556/436

Primary Examiner—Paul F. Shaver
Attorney, Agent, or Firm—Toren, McGeady & Stanger

[57] ABSTRACT

The invention provides a benzoin group-containing cyclic organopolysiloxane, which belongs to a novel class of organosilicon compounds hitherto not known or not described in any prior art literatures. The compound has at least one benzoin group of the formula

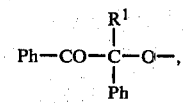

in which Ph is a phenyl group and $R^1$ is a hydrogen atom or an alkyl group having from 1 to 4 carbon atoms or, in particular, a methyl group, directly bonded to the silicon atom in the cyclic tri-, tetra-, penta- or hexasiloxane. The compound is useful as a sensitizer for the crosslinking reaction of a photo- or radiation-curable organopolysiloxane composition owing to the high miscibility of the inventive compounds with the organopolysiloxane composition.

8 Claims, 5 Drawing Figures

BENZOIN GROUP-CONTAINING CYCLIC ORGANOPOLYSILOXANES AND A METHOD FOR THE PREPARATION THEREOF

BACKGROUND OF THE INVENTION

The present invention relates to a novel cyclic organopolysiloxane or, more particularly, a novel cyclic organopolysiloxane having at least one benzoin group bonded to the silicon atom useful as a photosensitizer in accelerating photocuring of various kinds of photocurable resin compositions or, in particular, photocurable organopolysiloxane compositions as well as a method for the synthetic preparation of such a novel compound.

As is well known, almost all kinds of resin compositions curable by the irradiation with light or ionizing radiation such as high-energy electron beams are used as admixed with a photosensitizer in order to obtain an enhanced curing velocity by the irradiation. Several of the examples of the conventional photosensitizers are benzophenone, acetophenone, anthraquinone, benzanthrone, 4-nitrobiphenyl, 4-nitrophenol, 1,4-benzoquinone, 4,4'-dimethoxybenzophenone, N,N'-tetramethyl-4,4'-diaminobenzophenone (Michler's ketone), benzoin methyl ether and the like. When the photo- or radiation-curable resin composition is an organopolysiloxane composition as is disclosed in Japanese Patent Publications Nos. 53-36515, 52-31910, 53-2911, 53-5302, 52-40334, 54-6512, 54-43017 and 55-4770, certain disadvantages are encountered in the use of the above named organic compounds as the sensitizer since these organic compounds have rather limited miscibility with the organopolysiloxane. Namely, the photo- or radiation-curable organopolysiloxane compositions can contain only an insufficient amount of a sensitizer selected from the above named organic compounds so that the curable composition can be completely cured only by the irradiation for a relatively long period of time or uniformity of curing all over the irradiated surface is hardly ensured. When such a defective organopolysiloxane composition is used, for example, as a coating material of a peelable release paper, the sensitizer sometimes precipitates in the coating layer due to the poor miscibility with the organopolysiloxane disturbing the adhesion of the cured film to the substrate surface and the release paper cannot be imparted with satisfactory releasability.

With an object to overcome the above mentioned difficulties, several types of organosilicon compounds have been proposed as a sensitizer for photo- or radiation-curable organopolysiloxane compositions such as benzoin trialkylsilyl ethers (see Japanese Patent Publication No. 50-1597), silyl benzophenones (see Japanese Patent Publication No. 51-48794), benzoin group-containing organopolysiloxanes having a linear molecular chain structure (see Japanese Patent Kokai No. 54-44643) and the like.

These organosilicon compounds are still unsatisfactory as a sensitizer since the compounds of the former two classes have no sufficiently high miscibility with the organopolysiloxane compositions while, in the benzoin group-containing linear organopolysiloxanes, sufficient miscibility is obtained when the polysiloxane has a relatively large degree of polymerization but the content of the benzoin groups in such a high molecular polysiloxane cannot be so high relative to the other organic groups that a large amount thereof should be admixed in the photo- or radiation-curable composition leading to unavoidable decrease of the residual adhesion of the peelable release paper prepared by use of such a silicone composition.

Accordingly, there has been desired to develop a sensitizer for photo- or radiation-curable organopolysiloxane compositions having sufficient miscibility therewith and exhibiting satisfactory sensitizing effect even in a relatively small amount of addition.

SUMMARY OF THE INVENTION

The present invention therefore provides an organosilicon compound useful as a sensitizer for photo- or radiation-curable organopolysiloxane compositions free from the above described problems in the prior art sensitizer compounds, which compound belongs to a novel class of organosilicon compounds hitherto not known nor described in any literatures.

The invention also provides a novel method for the synthetic preparation of the above mentioned organosilicon compound.

The novel organosilicon compound is a benzoin group-containing cyclic organopolysiloxane represented by the general formula

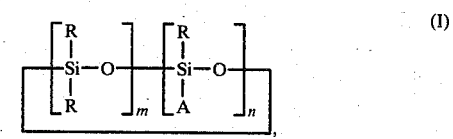

in which R is a substituted or unsubstituted monovalent hydrocarbon group, A is a benzoin group of the formula

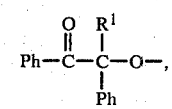

Ph being a phenyl group and $R^1$ being a hydrogen atom or an alkyl group having from 1 to 4 carbon atoms, m is zero or a positive integer and n is a positive integer with the proviso that m+n is 3, 4, 5 or 6.

The above described cyclic organopolysiloxane of the formula (I) can be prepared by reacting a benzoin or a derivative thereof expressed by AH, where A has the same meaning as defined above, with a cyclic organopolysiloxane represented by the general formula

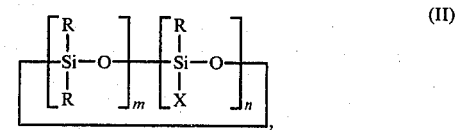

in which R, m and n each have the same meaning as defined above, and X is a hydrogen atom, a halogen atom, a hydroxy group or an alkoxy group having from 1 to 4 carbon atoms, in a suitable organic solvent.

DETAILED DESCRIPTION OF THE PREFERRED EMBODIMENTS

Figure 1:
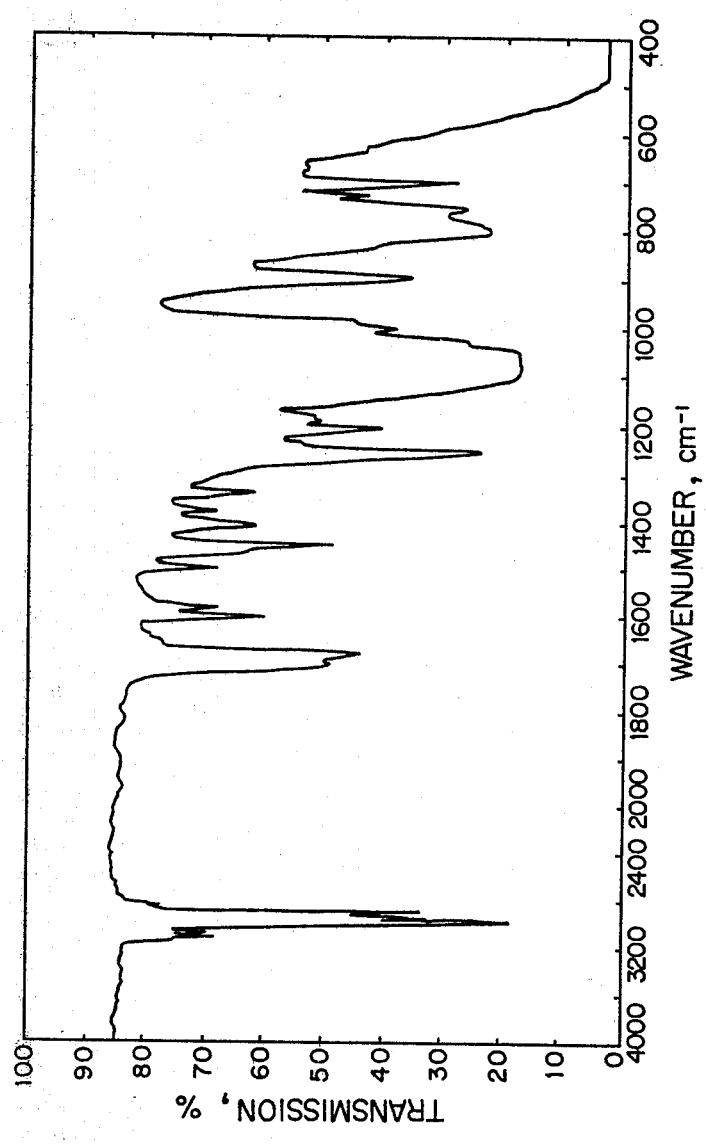
FIGS. 1 to 5 are each an infrared absorption spectrum of one of the inventive compounds prepared in the Examples.

The benzoin group-containing cyclic organopolysiloxanes of the present invention are expressed by the above given general formula (I). In the formula, the groups expressed by R are each independently a substituted or unsubstituted monovalent hydrocarbon group exemplified by alkyl groups such as methyl, ethyl, propyl and butyl groups, alkenyl groups such as vinyl and allyl groups, aryl groups such as phenyl, tolyl and xylyl groups and aralkyl groups such as benzyl and phenylethyl groups as well as those substituted groups having halogen atoms or other substituent atoms or groups in place of part or all of the hydrogen atoms in the above named hydrocarbon groups. The groups R in a molecule of the polysiloxane may be the same ones or different ones from each other.

The group A in the formula is a group derived from benzoin or an 2-substituted benzoin given by the formula above given, in which $R^1$ is a hydrogen atom or an alkyl group having from 1 to 4 carbon atoms, i.e. methyl, ethyl, propyl or butyl group. Generally speaking, $R^1$ is preferably a hydrogen atom or a methyl group for the reasons in the easiness of synthetic preparation of the inventive compound as well as usefulness as a sensitizer for the photo- or radiation-curable organopolysiloxane compositions.

The definitions of the suffixes m and n are as given above. Needless to say, the compound must contain at least one benzoin group A so that the suffix n cannot be zero. The value of m+n is 3, 4, 5 or 6 so that the compound is a cyclotri-, cyclotetra-, cyclopenta- or cyclohexasiloxane, respectively. This limitation is given in view of the compatibility of the inventive compound with the photo- or radiation-curable organopolysiloxane compositions. In particular, tetra- and pentasiloxanes are preferred or tetrasiloxanes are the most preferred owing to the easiness in the synthetic preparation.

When n in the formula (I) is larger than 2, i.e. the compound has three or more of the benzoin groups A in a molecule, the compatibility or miscibility of the compound with a photo- or radiation-curable organopolysiloxane composition is decreased so that the value of n is preferably 1 or 2.

Several of the examples of the inventive benzoin group-containing cyclic organopolysiloxanes are as follows. In the structural formulas given below and hereafter, the symbols Me, Et, Pr, Bu, Vi and Ph denote methyl, ethyl, propyl, butyl, vinyl and phenyl groups, respectively, and $A^1$ and $A^2$ denote each a benzoin group and methyl-substituted benzoin group of the formulas Ph—CO—CH—O— and Ph—CO—C(Me)—O—, respectively.
    |                        |
    Ph                       Ph

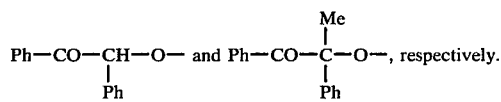

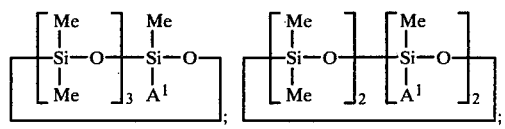

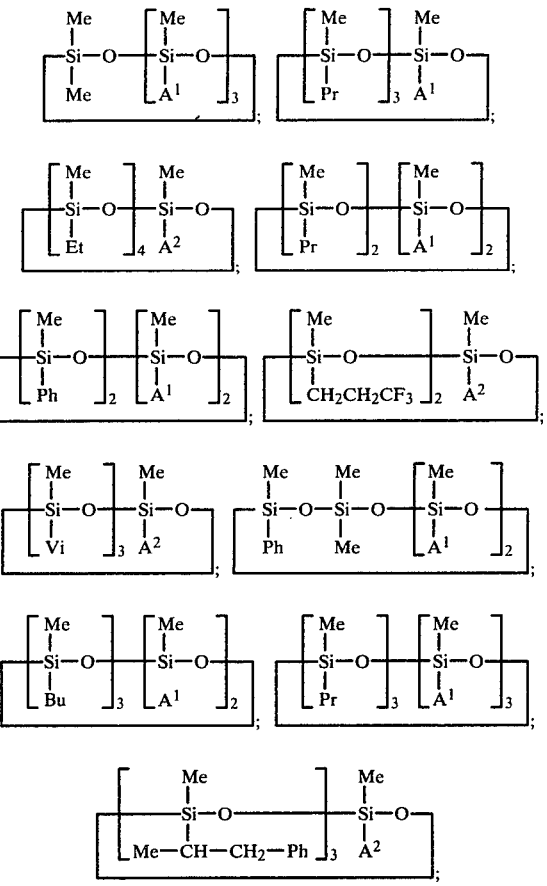

These benzoin group-containing cyclic organopolysiloxanes are synthesized, as is mentioned above, by the reaction of a benzoin compound of the formula AH or, in particular, benzoin or 2-methyl-benzoin of the formulas $A^1H$ or $A^2H$, respectively, with a functional cyclic organopolysiloxane of the formula (II) in a suitable organic solvent. The type of the reaction naturally depends on the functional group X in the formula (II), which may be a hydrogen atom, a halogen atom, a hydroxy group or an alkoxy group having from 1 to 4 carbon atoms. The amount of the benzoin compound as one of the reactants should be equimolar or larger to the functional groups X in the starting cyclic organopolysiloxane of the formula (II) as the other reactant.

The starting cyclic organopolysiloxanes of the formula (II) are known compounds and obtained by various methods. For example, the cyclic organopolysiloxanes in which the functional group X is a hydrogen atom can be prepared by the cohydrolysis and subsequent co-condensation reaction of an organohydrogendihalogenosilane and a diorganodihalogenosilane. Further, the cyclic organopolysiloxanes in which the functional group X is a halogen atom can be prepared by the reaction of a halogen with the above obtained cyclic organopolysiloxane having a hydrogen atom directly bonded to the silicon atom. The halogen atom directly bonded to the silicon atoms can be readily converted to a hydroxy group or an alkoxy group in a known method.

Following are several of the examples of the structural formulas of the cyclic organopolysiloxanes in conformity with the formula (II) suitable as the starting material of the inventive benzoin group-containing cyclic organopolysiloxanes.

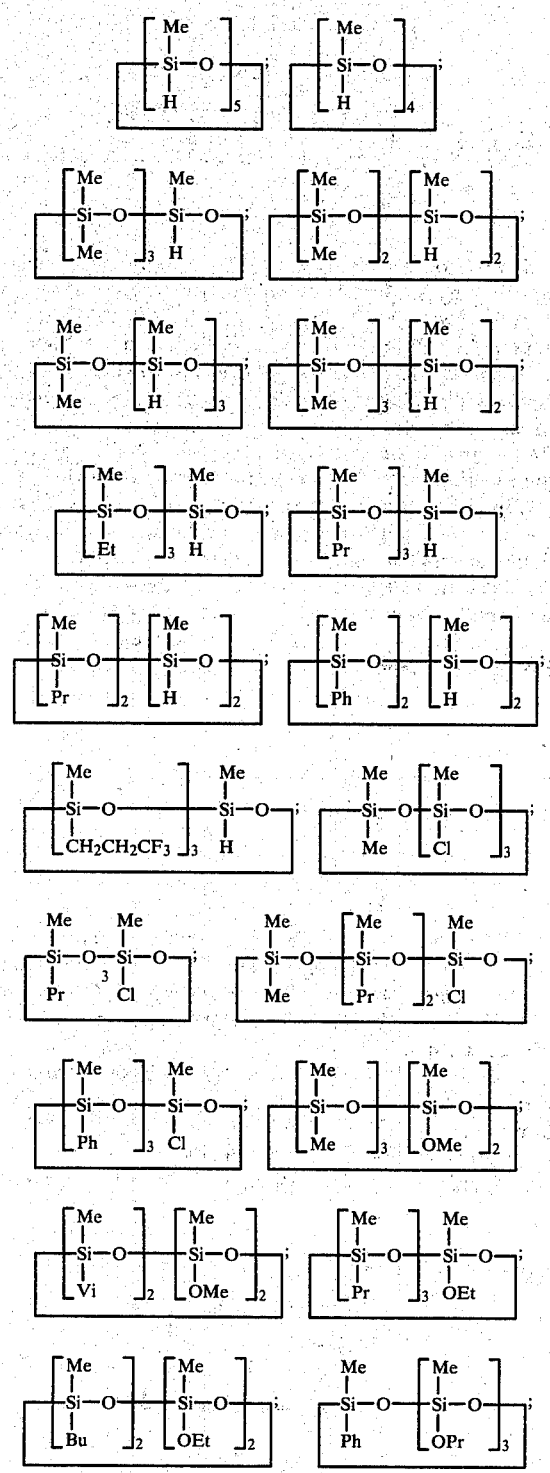

The reaction between the benzoin compound and the starting cyclic organopolysiloxane of the general formula (II) is carried out in a suitable organic solvent such as toluene, xylene, ether solvents, ketones and halogenated hydrocarbon solvents.

Usually, the reaction is carried out in the presence of a catalyst or other reaction-promoting agents depending on the type of the reaction. When the functional group X in the starting organopolysiloxane is a hydrogen atom, for example, the reaction is a dehydrogenation reaction and accelerated by a catalytic amount of zinc dust, sodium methylate, dibutyltin dilaurate, hydroxylamine or chloroplatinic acid as a catalyst. When the group X is a halogen atom, the reaction is a dehydrohalogenation reaction which is accelerated in the presence of an acid acceptor such as triethylamine, pyridine, dimethylaniline, urea and derivatives thereof and the like. When the group X is an alkoxy group, the reaction is a dealcoholation reaction and tin dioctoate, esters of titanic acid and the like are effective in promoting the reaction. The above reactions are undertaken at a temperature from room temperature to the boiling point of the organic solvent in the reaction mixture. After completion of the reaction, the catalyst or the by-product formed by the reaction such as an amine hydrohalide in the case of the dehydrohalogenation reaction is removed from the reaction mixture and then the organic solvent is removed by distillation to give the desired benzoin group-containing cyclic organopolysiloxane of the invention expressed by the formula (I).

The benzoin group-containing cyclic organopolysiloxanes of the present invention are effective as a sensitizer for various kinds of photo- or radiation-curable resin compositions and particularly useful for accelerating curing of photo- or radiation-curable organopolysiloxane compositions by virtue of the excellent compatibility or miscibility therewith. Specifically, the inventive compounds are useful as a photosensitizer of a photocurable organopolysiloxane composition composed of a thioacryloxyalkyl or thiocinnamoyloxyalkyl containing organopolysiloxane or a mercapto group-containing organopolysiloxane as combined with an aliphatically unsaturated group, e.g. vinyl and allyl groups, containing-organopolysiloxane used for coating of a peelable release paper and the like because the inventive compound can exhibit excellent sensitizing effect even in a small amount by virtue of the good miscibility and has no adverse effect on the releasability, residual adhesion and the like performance of the release paper.

The inventive benzoin group-containing cyclic organopolysiloxanes of the present invention may be used as a sensitizer either alone or as a combination of two kinds or more and further may be used as combined with other conventional sensitizer compounds.

In the following, examples are given for the synthetic preparation and characterization of the inventive benzoin group-containing cyclic organopolysiloxanes as well as for the illustration of the effectiveness of the inventive compounds as a sensitizer in a photo-curable organopolysiloxane composition. In the examples, the meaning of the symbols or abridgements is the same as defined above.

EXAMPLE 1

Into a flask of 500 ml capacity equipped with a dropping funnel were taken 63.6 g (0.3 mole) of benzoin, 94.95 g (0.3 mole) of heptamethylchlorocyclotetrasiloxane and 120 ml of toluene to form a reaction mixture, into which 33.3 g (0.33 mole) of triethylamine were added dropwise at room temperature through the dropping funnel. The reaction took place thereupon exothermically to show a temperature rise of 2° to 3° C. After completion of the addition of triethylamine, the reaction mixture was further agitated for 60 minutes at 60° to 70° C. to complete the reaction. Removal of the triethylamine hydrochloride formed in the dehydrochlorination reaction by filtration and then toluene by distillation gave 137.3 g of a liquid product.

The results of the analyses as shown below undertaken with this liquid product supported that the product was the benzoin group-containing cyclic tetrasiloxane of the formula below. The yield was about 93% of the theoretical.

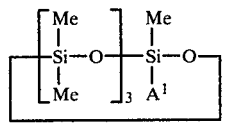

Physical properties and analytical results

| | |
|---|---|
| Boiling point: | 190 to 192° C./2 mmHg |
| Viscosity: | 55 centistokes at 25° C. |
| Refractive index: | 1.4889 at 25° C. |
| Infrared absorption spectrum (see FIG. 1): | |
| 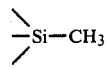 —Si—CH$_3$ | 1270, 810 and 705 cm$^{-1}$ |
| Aromatic ketone | three peaks in the region of 1800 to 2000 cm$^{-1}$ |
| Phenyl group | 1600, 1580 and 1450 cm$^{-1}$ |

Elementary analysis:

| | Found, % | Calculated as C$_{21}$H$_{32}$O$_6$Si$_4$, % |
|---|---|---|
| C | 50.8 | 51.22 |
| H | 6.6 | 6.51 |
| Si | 22.8 | 22.76 |

EXAMPLE 2

A reaction mixture was formed in a flask of 1 liter capacity by mixing 100 g (0.5 mole) of benzoin, 67 g (0.25 mole) of hexamethylcyclotetrasiloxane, 500 ml of ethyl acetate and 0.5 ml of an alcoholic solution of chloroplatinic acid in a concentration of 2% by weight as platinum and the dehydrogenation reaction was carried out by agitating the mixture for 6 hours at 70° to 80° C. with evolution of hydrogen gas. When the evolution of hydrogen gas had ceased, the solvent was removed by distillation from the reaction mixture to leave 154 g of a liquid product.

The results of the analyses as shown below undertaken with this liquid product supported that this product was the benzoin group-containing cyclic tetrasiloxane of the formula below. The yield was about 89% of the theoretical.

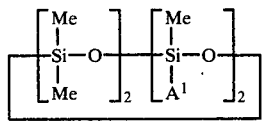

Physical properties and analytical results

| | |
|---|---|
| Viscosity: | 6950 centistokes at 25° C. |
| Refractive index: | 1.5302 at 25° C. |

Elementary analysis:

| | Found, % | Calculated as C$_{34}$H$_{40}$O$_8$Si$_4$, % |
|---|---|---|
| C | 59.0 | 59.30 |
| H | 5.1 | 5.81 |
| Si | 16.5 | 16.28 |

Infrared absorption

-continued

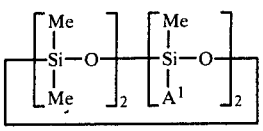

Physical properties and analytical results

Figure 2:
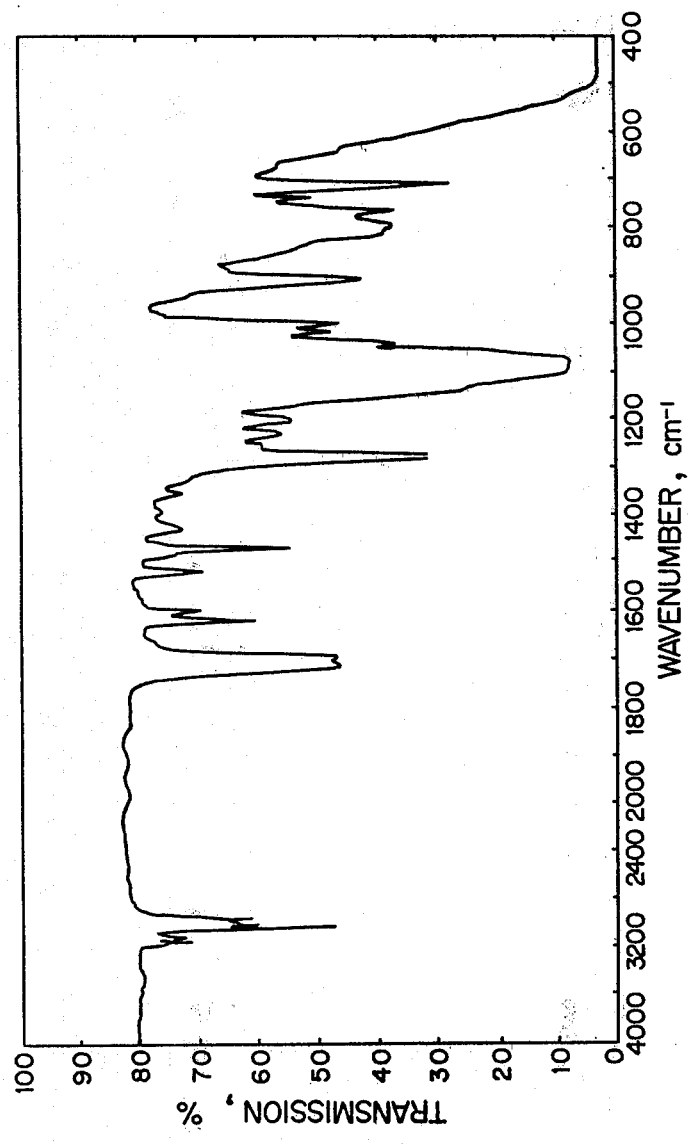

| | |
|---|---|
| spectrum: | (see FIG. 2) |

EXAMPLE 3

Figure 3:
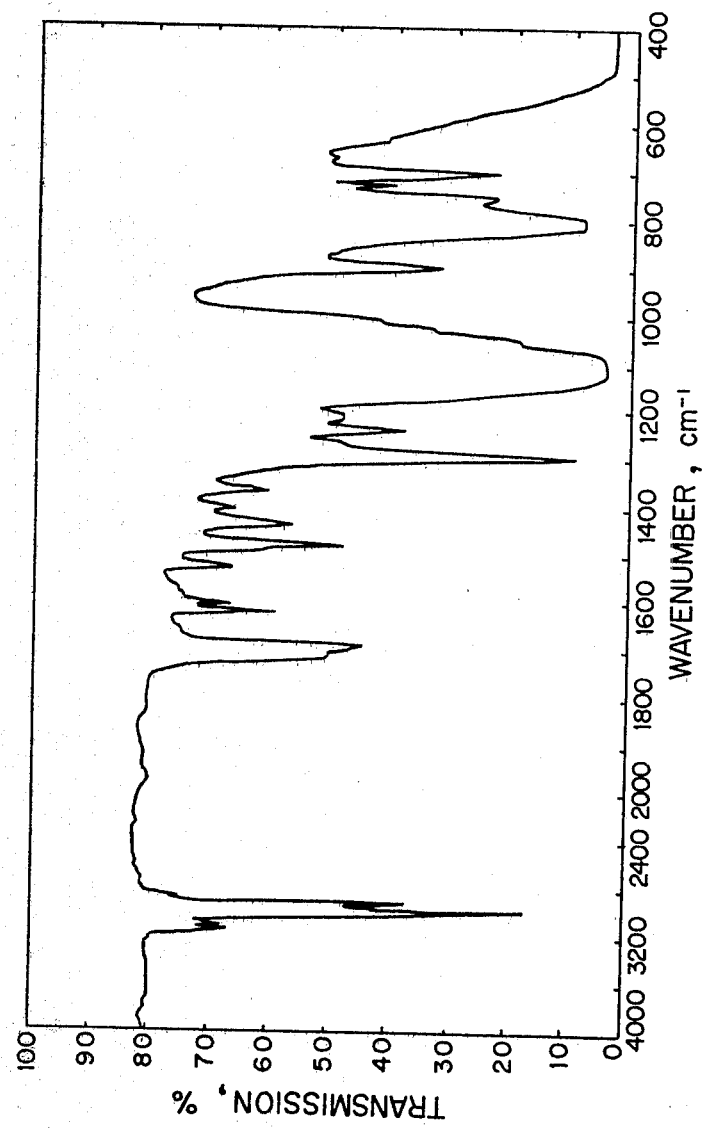

A reaction mixture was formed in a flask of 1 liter capacity by uniformly blending 67.8 g (0.3 mole) of 2-methylbenzoin, 124.2 g (0.3 mole) of 1,1,3,3,5,5,7,7-octamethyl-9-n-propyl-9-methoxycyclopentasiloxane, 0.1 g of tin dioctoate and 200 ml of toluene and the mixture was heated for 4 hours with agitation under reflux of toluene to effect the dealcoholation reaction. Removal of toluene and the methyl alcohol formed by the reaction from the reaction mixture gave 151 g of a yellow liquid product boiling at 195° to 199° C. under a pressure of 1 mmHg. Results of the analyses of this liquid product including the infrared absorption spectral analysis (see FIG. 3) supported that this product was the benzoin group-containing cyclopentasiloxane of the following formula. The above yield was about 83% of the theoretical.

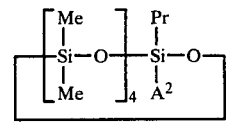

EXAMPLES 4 TO 8

Figure 4:
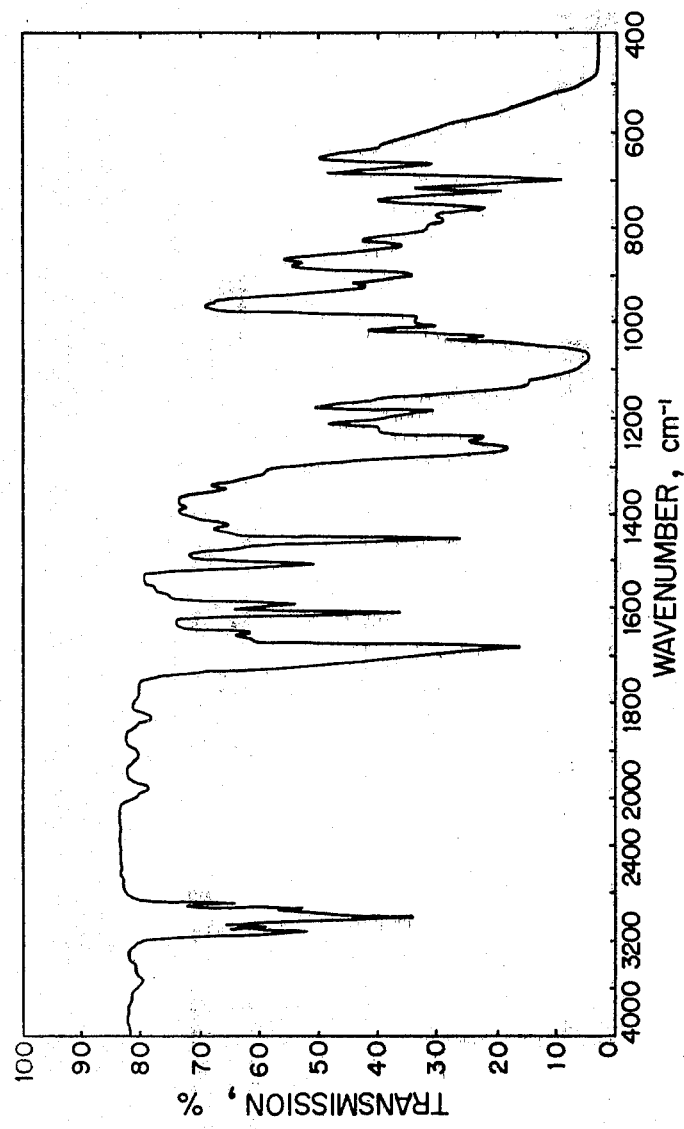
Figure 5:
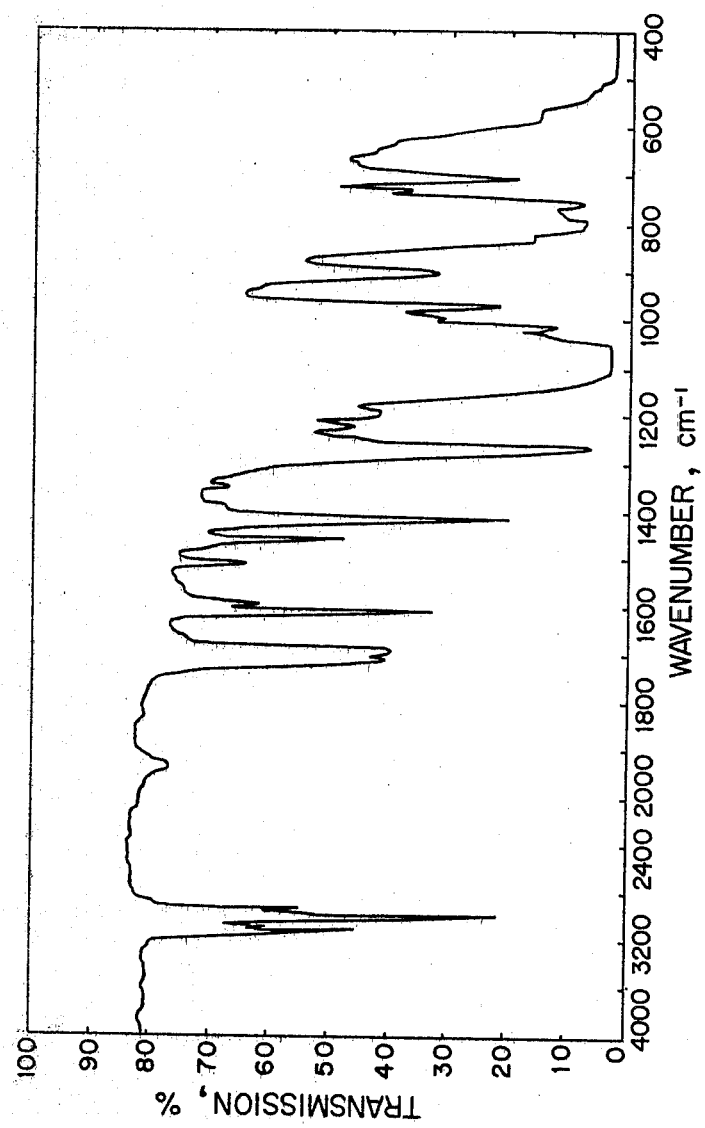

The benzoin group-containing cyclic organopolysiloxanes of the following formulas were prepared each in substantially the same manner as in Example 1 except that the heptamethylchlorocyclotetrasiloxane was replaced with a corresponding chlorine-containing cyclopolysiloxane. The viscosity, boiling point, results of the elementary analysis and the yield of the objective compound are shown in Table 1 below. The infrared absorption spectra of the compounds prepared in Examples 4 and 6 are shown in FIGS. 4 and 5, respectively.

Structural formulas of the compounds

Example 4:

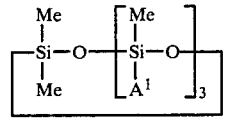

Example 5:

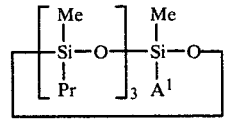

Example 6:

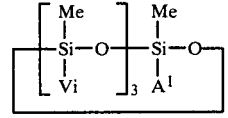

-continued
Structural formulas of the compounds

Example 7:

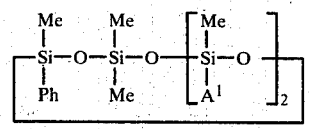

Example 8:

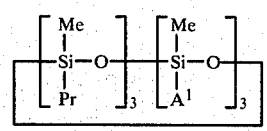

TABLE 1

| Example No. | Viscosity at 25° C. | Boiling point | Results of elementary analysis, % found (calculated) | | | Yield, % |
|---|---|---|---|---|---|---|
| | | | C | H | Si | |
| 4 | 15,000 centistokes | — | 62.1 (63.80) | 5.0 (5.43) | 13.7 (12.67) | 87 |
| 5 | 60 centistokes | 198–200° C. /2 mmHg | 52.0 (53.08) | 6.2 (6.92) | 21.7 (21.54) | 94 |
| 6 | 64 centistokes | 195–199° C. /3 mmHg | 50.2 (52.38) | 6.0 (6.35) | 21.8 (22.22) | 92 |
| 7 | 11,700 centistokes | — | 62.0 (62.40) | 5.0 (5.60) | 14.7 (14.93) | 88 |
| 8 | 54,400 centistokes | — | 59.3 (61.29) | 6.5 (6.45) | 17.0 (15.06) | 84 |

EXAMPLE 9

A photocurable organopolysiloxane composition was prepared by uniformly blending 100 parts by weight of a diorganopolysiloxane having a linear molecular structure as composed of 92% by moles of dimethylsiloxane units, 5% by moles of methylvinylsiloxane units and 3% by moles of diphenylsiloxane units and endblocked at both molecular chain ends with vinyldimethylsilyl groups with a viscosity of 1850 centistokes at 25° C., 10 parts by weight of a mercaptopropyl-containing organopolysiloxane composed of 50% by moles of dimethylsiloxane units and 50% by moles of 3-mercaptopropylsiloxane units $(HSCH_2CH_2CH_2)SiO_{1.5}$ with a viscosity of 150 centistokes at 25° C. and 0.05 part by weight of 2,6-di-tert-butyl-4-cresol.

The above prepared organopolysiloxane composition was admixed with either one of the benzoin group-containing cyclic organopolysiloxanes prepared in Examples 1 to 7 above, benzophenone or a benzoin group containing linear dimethylpolysiloxane each in an amount indicated in Table 2 below.

A polyethylene-laminated kraft paper was coated with one of the above prepared sensitized photocurable organopolysiloxane compositions uniformly in a coating amount of 0.8 g/m². The thus coated surface was irradiated with ultraviolet light emitted from two tubular mercury lamps of each 2 kilowatt power placed side by side by moving the coated kraft paper at varied velocities 80 mm below the lamps. The intensity of the light was 186 watts/cm² just below the center line of the two lamps and 53 watts/cm² at the area 2.5 cm apart from the center line. The irradiation time was calculated as the time interval during which the moving kraft paper traversed 5 cm width below the lamps as shown in Table 2 corresponding to varied irradiation dose. The irradiation time given in the table is the minimum time at which completely photo-cured coating film of the organopolysiloxane composition was obtained exhibiting reproducible releasability characteristics as examined by the procedure specified in JIS Z 1523 to give the results shown in Table 2.

The molecular structure of the benzoin-containing linear dimethylpolysiloxane was as shown by the following formula;

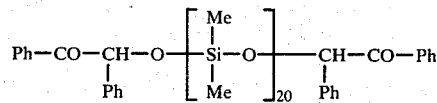

and the miscibility thereof with the organopolysiloxane composition was good when the amount of addition was 2.0 parts by weight while 5.0 parts by weight thereof gave slight cloudiness to the organopolysiloxane composition. Meanwhile, the miscibility of the inventive compounds with the organopolysiloxane composition was good each to give a clear photosensitized composition when the amount of addition was 1.0 part by weight while admixing of benzophenone resulted in cloudy organopolysiloxane composition when the amount of addition was 1.0 part by weight or more indicating poor compatibility of benzophenone with the organopolysiloxane composition.

As is understood from the results shown in Table 2, the inventive benzoin group-containing cyclic organopolysiloxanes have much better miscibility with the organopolysiloxane composition to exhibit higher photosensitizing effect than the known sensitizers and can give particularly excellent releasability characteristics and residual adhesion to the peelable release paper prepared therewith.

TABLE 2

| Photosensitizer | Amount added, parts by weight | Minimum cure time, seconds | Peeling resistance, g/5 cm* | Residual adhesion, % |
|---|---|---|---|---|
| Example 1 | 1.0 | 0.1 | 170 | 95 |
| Example 2 | 1.0 | 0.06 | 188 | 95 |
| Example 3 | 1.0 | 0.1 | 160 | 98 |
| Example 4 | 1.0 | 0.03 | 190 | 95 |
| Example 5 | 1.0 | 0.06 | 220 | 93 |
| Example 6 | 1.0 | 0.1 | 200 | 97 |
| Example 7 | 1.0 | 0.06 | 170 | 93 |
| Benzophenone | 2.0 | 0.6 | 280 | 70 |
| Benzophenone | 1.0 | 1.2 | 350 | 65 |
| Benzoin-containing dimethylpolysiloxane | 5.0 | 0.06 | 100 | 81 |
| Benzoin-containing dimethylpolysiloxane | 2.0 | 0.2 | 150 | 75 |

*Rubber-based adhesive agent

EXAMPLE 10

Photocurable organopolysiloxane compositions were prepared each by uniformly blending 90 parts by weight of a thioacryloxy-containing diorganopolysiloxane composed of 97% by moles of dimethylsiloxane units and 3% by moles of methyl thioacryloxypropyl siloxane units ($CH_2$=CHCOSCH$_2$CH$_2$CH$_2$)MeSiO and end-blocked at both molecular chain ends with trimethylsilyl groups with a viscosity of 890 centistokes at 25° C., 10 parts by weight of a mercaptopropyl-containing organopolysiloxane composed of 50% by moles of dimethylsiloxane units and 50% by moles of 3-mercaptopropylsiloxane units (HSCH$_2$CH$_2$CH$_2$)SiO$_{1.5}$ with a viscosity of 150 centistokes at 25° C., 0.05 part by weight of 2,6-di-tert-butyl-4-cresol and 1.0 part by weight of either one of the benzoin group-containing cyclic organopolysiloxanes prepared in Examples 1 to 5.

For comparison, similar compositions were prepared with the same formulation as above except that 2.0 parts by weight of benzoin methyl ether or benzoin trimethylsilyl ether were used as the photosensitizer in place of the above mentioned cyclic organopolysiloxanes.

A glassine paper was coated with the above prepared photo-curable organopolysiloxane composition uniformly in a coating amount of 1.0 g/m$^2$ and the minimum cure time was determined by use of the same apparatus for ultraviolet irradiation as used in Example 9. Further, the releasability characteristics and the adhesion to the substrate, i.e. rub-off resistance, of the cured coating films were examined according to JIS Z 1523 to give the results shown in Table 3.

As is understood from the results given in Table 3, the inventive benzoin group-containing cyclic organopolysiloxanes are effective in photosensitizing the thioacryloxy-containing photo-curable organopolysiloxane composition and good photosensitizing effect is obtained with a small amount of addition thereof due to the high miscibility to give cured coating films with high adhesion exhibiting excellent releasability characteristics or, in particular, residual adhesion within a remarkably short irradiation time.

What is claimed is:

1. A benzoin group-containing cyclic organopolysiloxane represented by the general structural formula

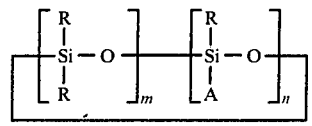

in which R is a substituted or unsubstituted monovalent hydrocarbon group, A is a benzoin group expressed by the formula

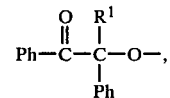

Ph being a phenyl group and $R^1$ being a hydrogen atom or an alkyl group having from 1 to 4 carbon atoms, m is zero or a positive integer and n is a positive integer with the proviso that m+n is 3, 4, 5 or 6.

2. The benzoin group-containing cyclic organopolysiloxane as claimed in claim 1 wherein $R^1$ is a hydrogen atom or a methyl group.

3. The benzoin group-containing cyclic organopolysiloxane as claimed in claim 1 wherein m+n is 4 or 5 and n is 1 or 2.

4. The benzoin group-containing cyclic organopolysiloxane as claimed in claim 1 wherein R is a methyl group.

5. A method for the preparation of a benzoin group-containing cyclic organopolysiloxane represented by the general structural formula

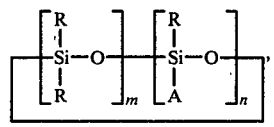

in which R is a substituted or unsubstituted monovalent hydrocarbon group, A is a benzoin group expressed by the formula

TABLE 3

| Photo-sensitizer | Amount of addition, parts by weight | Minimum cure time, seconds | Peeling resistance, g/5 cm, with | | Residual adhesion, % | Adhesion of cured film |
|---|---|---|---|---|---|---|
| | | | Rubber-based adhesive | Arcylic emulsion-type adhesive | | |
| Example 1 | 1.0 | 0.06 | 75 | 18 | 98 | Good |
| Example 2 | 1.0 | 0.06 | 70 | 17 | 96 | Good |
| Example 3 | 1.0 | 0.10 | 80 | 20 | 94 | Good |
| Example 4 | 1.0 | 0.06 | 72 | 15 | 96 | Good |
| Example 5 | 1.0 | 0.06 | 69 | 19 | 97 | Good |
| Benzoin methyl ether | 2.0 | 0.2 | 35 | 15 | 65 | Readily rubbed off |
| Benzoin trimethyl silyl ether | 2.0 | 0.2 | 65 | 20 | 70 | Partly rubbed off |

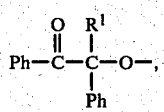

Ph being a phenyl group and $R^1$ being a hydrogen atom or an alkyl group having from 1 to 4 carbon atoms, m is zero or a positive integer and n is a positive integer with the proviso that m+n is 3, 4, 5 or 6, which comprises reacting a benzoin compound of the formula AH, in which A has the same meaning as defined above, with a functional cyclic organopolysiloxane represented by the general structural formula

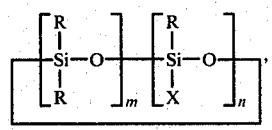

in which R, m and n each have the same meaning as defined above and X is a hydrogen atom, a halogen atom, a hydroxy group or an alkoxy group having from 1 to 4 carbon atoms, in an organic solvent in the presence of a reaction-promoting agent.

6. The method as claimed in claim 5 wherein X is a hydrogen atom and the reaction-promoting agent is selected from the class consisting of zinc dust, sodium methylate, dibutyltin dilaurate, hydroxylamine and chloroplatinic acid.

7. The method as claimed in claim 5 wherein X is a halogen atom and the reaction-promoting agent is an acid acceptor selected from the class consisting of triethylamine, pyridine, dimethylaniline, urea and a derivative thereof.

8. The method as claimed in claim 5 wherein X is an alkoxy group and the reaction-promoting agent is tin dioctoate or an ester of titanic acid.

* * * * *